US010849705B1

United States Patent
LaBua

(10) Patent No.: US 10,849,705 B1
(45) Date of Patent: Dec. 1, 2020

(54) STORAGE RACK FOR USE WITH A MEDICAL SLIDE BRACKET FOR HOLDING AND SUPPORTING ACCESSORY ARTICLES

(71) Applicant: Steven LaBua, Katy, TX (US)

(72) Inventor: Steven LaBua, Katy, TX (US)

( * ) Notice: Subject to any disclaimer, the term of this patent is extended or adjusted under 35 U.S.C. 154(b) by 0 days.

(21) Appl. No.: 16/840,413

(22) Filed: Apr. 5, 2020

Related U.S. Application Data

(60) Provisional application No. 62/830,424, filed on Apr. 6, 2019.

(51) Int. Cl.
*A61B 50/22* (2016.01)
*A61M 1/00* (2006.01)

(52) U.S. Cl.
CPC ........... *A61B 50/22* (2016.02); *A61M 1/0001* (2013.01); *A61M 2207/00* (2013.01); *A61M 2209/082* (2013.01)

(58) Field of Classification Search
CPC .......... A61M 1/0001; A61M 2209/082; A61M 2207/00; A47F 5/01; A47F 5/0031; A47F 7/148; A47F 3/147; F16M 11/04; F16M 11/12; A61B 50/22; D06F 57/12
USPC ......... 211/181.1, 85.13, 85.29, 85.31, 87.01, 211/119, 119.009; 248/122.1, 689, 176.1, 248/205.1, 220.21, 220.22, 224.7, 226.11, 248/309.1, 316.1
See application file for complete search history.

(56) References Cited

U.S. PATENT DOCUMENTS

| | | | | |
|---|---|---|---|---|
| 269,538 A | * | 12/1882 | Randall | A47G 25/10 211/32 |
| D27,014 S | * | 5/1897 | Sully | D6/678.4 |
| 4,387,811 A | * | 6/1983 | Ragir | A47B 55/02 211/106 |
| 4,662,524 A | * | 5/1987 | Fullenkamp | A47B 57/565 211/190 |
| D315,840 S | * | 4/1991 | Emery | D6/525 |
| 5,080,238 A | * | 1/1992 | Hochman | A47F 5/0869 211/106.01 |
| D367,790 S | * | 3/1996 | Munoz | D6/513 |
| 5,537,289 A | | 7/1996 | Dahl | |
| D376,941 S | * | 12/1996 | Munoz | D23/309 |
| 5,683,010 A | * | 11/1997 | Boyajian, Jr. | A47J 36/12 220/744 |
| D400,745 S | * | 11/1998 | France | D6/525 |

(Continued)

*Primary Examiner* — Jonathan Liu
*Assistant Examiner* — Devin K Barnett
(74) *Attorney, Agent, or Firm* — Kenneth A. Roddy

(57) ABSTRACT

A storage rack formed of rigid rod for removably mounting on a medical slide bracket has an elongated, inverted generally U-shaped support member having a pair of elongated laterally opposed leg portions with hook portions at a bottom end, and an inverted generally U-shaped holder member having a pair of laterally opposed upper leg portions with intermediate angular lower leg portions secured to the leg portions of the support member. The holder member upper leg portions, and intermediate angular lower leg portions are disposed forwardly of the top portion and vertical legs of the support member defining an open storage area between the holder member and the support member. The support member is configured to be removably supported on the slide bracket, and the open storage area between the holder member and support member, and the hook portions are adapted to receive and store medical supplies and equipment.

3 Claims, 3 Drawing Sheets

(56) References Cited

U.S. PATENT DOCUMENTS

| | | | | |
|---|---|---|---|---|
| 6,065,613 A * | 5/2000 | Gusdorf | A47F 7/08 | 211/119 |
| 6,089,387 A * | 7/2000 | Varfolomeeva | A47B 57/06 | 211/106 |
| 6,386,379 B1 * | 5/2002 | Battaglia | A47B 96/00 | 211/106 |
| 6,464,087 B1 * | 10/2002 | Klein | A47B 96/16 | 211/113 |
| 6,484,747 B2 * | 11/2002 | Bridgers | A61M 16/08 | 128/204.18 |
| 6,520,351 B1 * | 2/2003 | Zadro | A47K 3/281 | 211/106 |
| D473,084 S * | 4/2003 | Suero, Jr. | A47K 3/281 | D6/525 |
| 6,564,950 B1 * | 5/2003 | Holm | A47B 55/02 | 211/106 |
| 6,729,479 B2 * | 5/2004 | Morgan | A47J 47/16 | 211/41.11 |
| 7,090,085 B1 * | 8/2006 | Vicendese | A47F 5/08 | 211/106.01 |
| 7,270,309 B2 * | 9/2007 | Burns | F16M 13/02 | 211/162 |
| D564,271 S * | 3/2008 | Snider | A47K 3/281 | D6/525 |
| D564,816 S * | 3/2008 | Snider | A47K 3/281 | D6/525 |
| D568,657 S * | 5/2008 | Snider | A47K 3/281 | D6/525 |
| D572,061 S * | 7/2008 | Snider | A47K 3/281 | D6/525 |
| D572,062 S * | 7/2008 | Snider | A47K 3/281 | D6/525 |
| 7,527,157 B2 * | 5/2009 | Shinn | B25H 3/006 | 211/119 |
| 7,611,034 B1 * | 11/2009 | Peterson | A47G 25/743 | 223/88 |
| 7,871,581 B1 * | 1/2011 | Coleman | A61L 2/26 | 422/300 |
| D632,514 S * | 2/2011 | Didehvar | A47K 3/281 | D6/525 |
| 7,959,020 B2 * | 6/2011 | Rosen | D06F 79/02 | 211/119.001 |
| 9,345,322 B1 * | 5/2016 | Starnes | B60R 7/10 | |
| 10,064,523 B2 * | 9/2018 | Engell | A47K 3/281 | |
| 2002/0092817 A1 * | 7/2002 | Lamb | A47K 3/281 | 211/119 |
| 2002/0148795 A1 * | 10/2002 | Miller, Jr. | A47F 3/0486 | 211/88.01 |
| 2003/0168417 A1 * | 9/2003 | Morgan | A47F 5/01 | 211/41.11 |
| 2005/0284991 A1 | 12/2005 | Saez | | |
| 2006/0261021 A1 * | 11/2006 | Stagnaro | A47F 5/0884 | 211/119 |
| 2008/0047913 A1 * | 2/2008 | Naden | A47K 3/281 | 211/119.009 |
| 2008/0053935 A1 * | 3/2008 | Newbouild | A47B 96/1408 | 211/90.02 |
| 2011/0168857 A1 * | 7/2011 | Svedman | A61M 1/0088 | 248/218.4 |
| 2015/0325991 A1 | 11/2015 | Allen | | |

\* cited by examiner

US 10,849,705 B1

STORAGE RACK FOR USE WITH A MEDICAL SLIDE BRACKET FOR HOLDING AND SUPPORTING ACCESSORY ARTICLES

CROSS REFERENCE TO RELATED APPLICATION

This application claims priority of U.S. Provisional Application Ser. No. 62/830,424, filed on Apr. 6, 2019.

BACKGROUND OF THE INVENTION

1. Field of the Invention

This invention relates generally to the storing of equipment, such as medical equipment, and more particularly, to a storage rack configured to be removably mounted on a conventional medical slide bracket of the type employed in hospitals for supporting a vacuum collection container whereby the rack safely stores and supports various accessory medical articles for reliable, rapid, ready access by medical personnel as needed.

2. Background Art

Currently in hospitals and health care facilities such as surgery centers, emergency rooms, clinics, etc., patient care supplies, wires, cables and/or tubing, are commonly coiled and hung on medical gas flowmeters that protrude from gas outlets mounted in the wall of the hospital room. Accessory items and supplies are also often wedged between the wall and flowmeters attached to the gas outlets until ready for use.

The supplies are usually bagged and sometimes sterile in the packaging. It is not uncommon for personnel to puncture bags so they can hang on the flowmeters. Although the packaged items may be readily available, the sterility of the bagged item may be jeopardized. Supplies bagged in drawstring bags and resuscitator bags are also often hung from flowmeters. However, this practice can cause premature wear to medical gas outlets that are costly to repair and maintain. When the outlets become worn they often leak or have the potential to not function properly. Leaking outlets cost the facility money in lost product and lead to increased equipment run time, equipment wear, preventative maintenance, and energy usage. Gas leaks are not only costly due to product loss but also present a fire hazard. Worn or damaged outlets are a nuisance to nursing staff and can have detrimental outcomes for patient care due to flowmeters or hoses not locking in securely or functioning properly when urgent care is necessary.

In some instances, hooks are drilled or taped to the wall of the room. However, this presents the possibility for an infection control issue and requires hospital personnel to drill into a wall containing numerous utilities. After time sheet rock anchors become loose and expose damaged sheet rock. The sheet rock dust caused from this presents infection risk for patients. When doubled sided tape is used to stick a hook to the wall it sometimes removes the paint that it adhered to and leaves the sheet rock exposed with the potential for the same infection issue. To repair even minor sheetrock issues, a room has to be blocked/removed from service for sanding and painting which leaves the facility temporarily without use of a licensed bed.

Fullenkamp, et al, U.S. Pat. No. 4,662,524, discloses a free-standing medical service column having front and rear chases with service outlets mounted on at least the front side for connection with fluid and electrical conduits. The column includes vertically extending tracks at each corner that extend substantially the height of the column. Brackets, holders, and equipment are connected to the tracks by means of locking slide assemblies. Each slide assembly includes a base and a slide element formed of a low-friction material. A screw interconnects the base with the slide element such that rotation of the screw moves the slide toward the base and against the wall of the channel to frictionally secure the slide within the channel. Members secured to the column by means of locking slide elements may also carry a bracket. The bracket includes a plug formed of resilient material, which is received in a cylindrical bore of the member. When the bracket is rotated to a desired position of adjustment, the plug is expanded radially outwardly into frictional engagement with a wall of the bore to affix the bracket immovably to the member.

Dahl, U.S. Pat. No. 5,537,289, discloses a medical monitoring system with removable modules which includes a wall mounting plate to which a center support member is rigidly attached using a pair of mounting flanges that engage a pair of integral tracks on a forward surface of the mounting plate. The center support supports a plurality of module housings, each of which contains module slots for insertion of interchangeable modular components. A touch-screen display mounts to the center support member using a pedestal which permits rotation of the display in two orthogonal directions to permit ease of viewing by a user. An electronic device such as a power supply may be mounted to the tracks with mounting brackets to provide power for the monitoring system. A pair of secondary tracks on the mounting plate support a cable retainer and provide a passageway for cables to pass beneath the power supply where they are concealed from view.

Bridgers, U.S. Pat. No. 6,484,747, discloses a medical gas utility stand for connection to at least one remote medical gas source, each medical gas source detachably connectable to a gas conduit line so that the gas conduit line is in fluid communication with one medical gas source. The gas utility stand includes a base connected to a substantially upright support member, and a gas connection member having at least one gas conduit defining a gas passage extending between an input end and an output end, the gas connection member fixedly connected to the support member adjacent its top end. In one embodiment, the gas utility stand includes a mounting plate detachably connected to the support member intermediate the base and the gas connection member having a front surface, a back surface, and a plurality of slide brackets attached to the front surface in a substantially upright orientation.

Saez, U.S. Published Patent Application 2005/0284991, discloses a mechanism for positional adjustment of an attached device, such as a display or input device. In one embodiment, the mechanism is a front end height adjustment mechanism comprising a track apparatus, a display mounting bracket, a slide bracket, and a motion regulating device.

Allen, U.S. Published Patent Application 2015/0325991 discloses a trim plate with retractable hook arm that includes a base plate, a folding hook arm pivotally attached to the base plate, and a weight-bearing truss that supports the folding hook arm. A first end of the weight bearing truss is pivotally connected to the hook arm at about the middle of the hook arm and the second end of the truss is positioned in a primary slot in the base plate. Two secondary slots in the base plate are positioned on either side of the primary slot, and pins extend perpendicularly from the base plate end of the truss and fit in the secondary slots for sliding therein whenever the hook arm is open or closed.

SUMMARY OF THE INVENTION

The present invention overcomes the aforementioned problems and is distinguished over the prior art in general, and these patents in particular by a storage rack for removably mounting on a medical slide bracket of the type used to support a vacuum canister that collects mucous, gas, or fluid aspirated from a patient, the slide bracket having a flat back wall engaged on a support surface and laterally opposed vertical curved sides that curve outwardly and forwardly from the back wall terminate in a short inwardly curved portion to form a pair of vertical channels.

The storage rack includes a support member and a holder member formed of rigid metal or plastic rod material. The support member is an elongated, inverted generally U-shaped support member having a horizontal top portion, a pair of elongated laterally opposed leg portions extending vertically downward from each end thereof and terminating in respective outwardly extending hook portions at a bottom end, and a thin flat T-shaped tab secured between the laterally opposed leg portions a distance above the hook portions.

The holder member is an inverted generally U-shaped holder member having an elongated, inverted generally U-shaped horizontal portion at a top end, a pair of elongated laterally opposed upper leg portions extending vertically downward a distance from each end thereof, each having an intermediate angular lower leg portion extending a distance angularly downwardly and rearwardly therefrom terminating in respective short vertical leg portions secured to the laterally opposed leg portions of the support member a distance above the T-shaped tab. The holder member horizontal top portion, upper leg portions, and intermediate angular lower leg portions are disposed a distance forward of the horizontal top portion and the vertical legs of the support member above the thin T-shaped tab, defining an open storage area between the holder member and the support member.

The elongated laterally opposed leg portions of the support member are configured to straddle the back wall of the slide bracket, and the thin flat T-shaped tab secured between the laterally opposed leg portions is configured to engage and be supported on top ends of the laterally opposed vertical outer curved sides of the slide bracket.

The open storage area between the holder member vertical upper leg and intermediate angular lower leg portions and the support member vertical legs, and the hook portions at the bottom end of the support member legs are adapted to receive and store medical supplies and equipment.

One of the differences and advantages of the present invention is that the storage rack is easily and installed on and removed from an existing conventional medical slide bracket without the use of tools, fasteners, or special equipment.

Another difference and advantage of the present invention is that when the storage rack is installed on the conventional slide bracket it does not interfere with the use of the slide bracket to support a vacuum canister that collects mucous, gas, or fluid aspirated from a patient.

Another difference and advantage of the present invention is that when the storage rack is installed on the conventional slide bracket, the open storage area between the vertical upper leg portions and intermediate angular lower leg portions of the holder member may be used for removably receiving and supporting various accessory medical articles such as, multiple and various sizes of bags and packaged items, and supplies bagged in drawstring bags and resuscitator bags as well as hoses and electrical cords may be hung from the hooked portions at the bottom ends of the legs of the support member, placing them in convenient ready access by medical personnel as needed.

Other differences and advantages of the invention will become apparent from time to time throughout the specification and claims as hereinafter related.

DETAILED DESCRIPTION OF THE INVENTION

Figure 1:
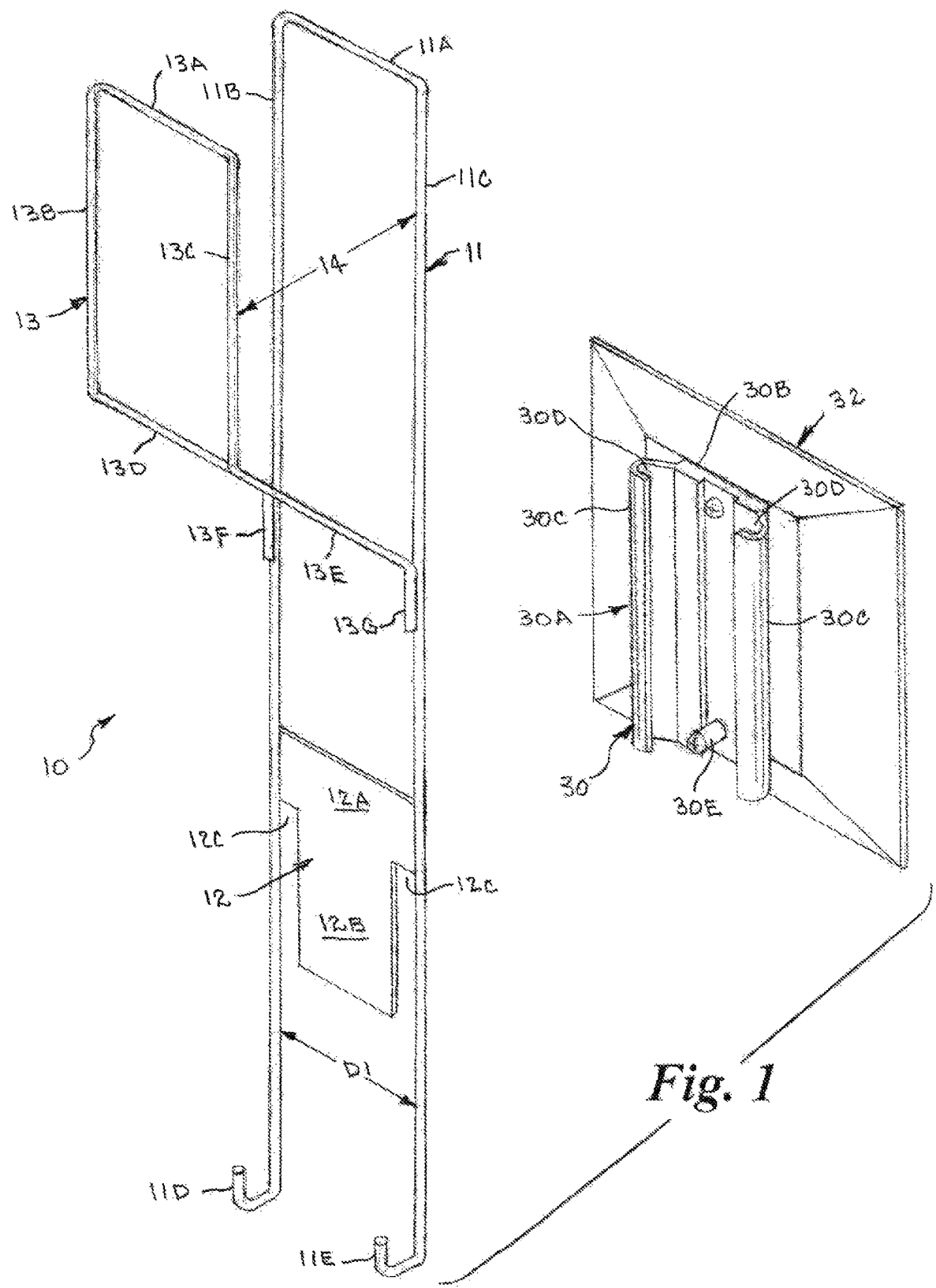
FIG. 1 is an exploded perspective view of the storage rack in accordance with the present invention for removably mounting on a conventional medical slide bracket shown adjacent to the rack.
Figure 2:
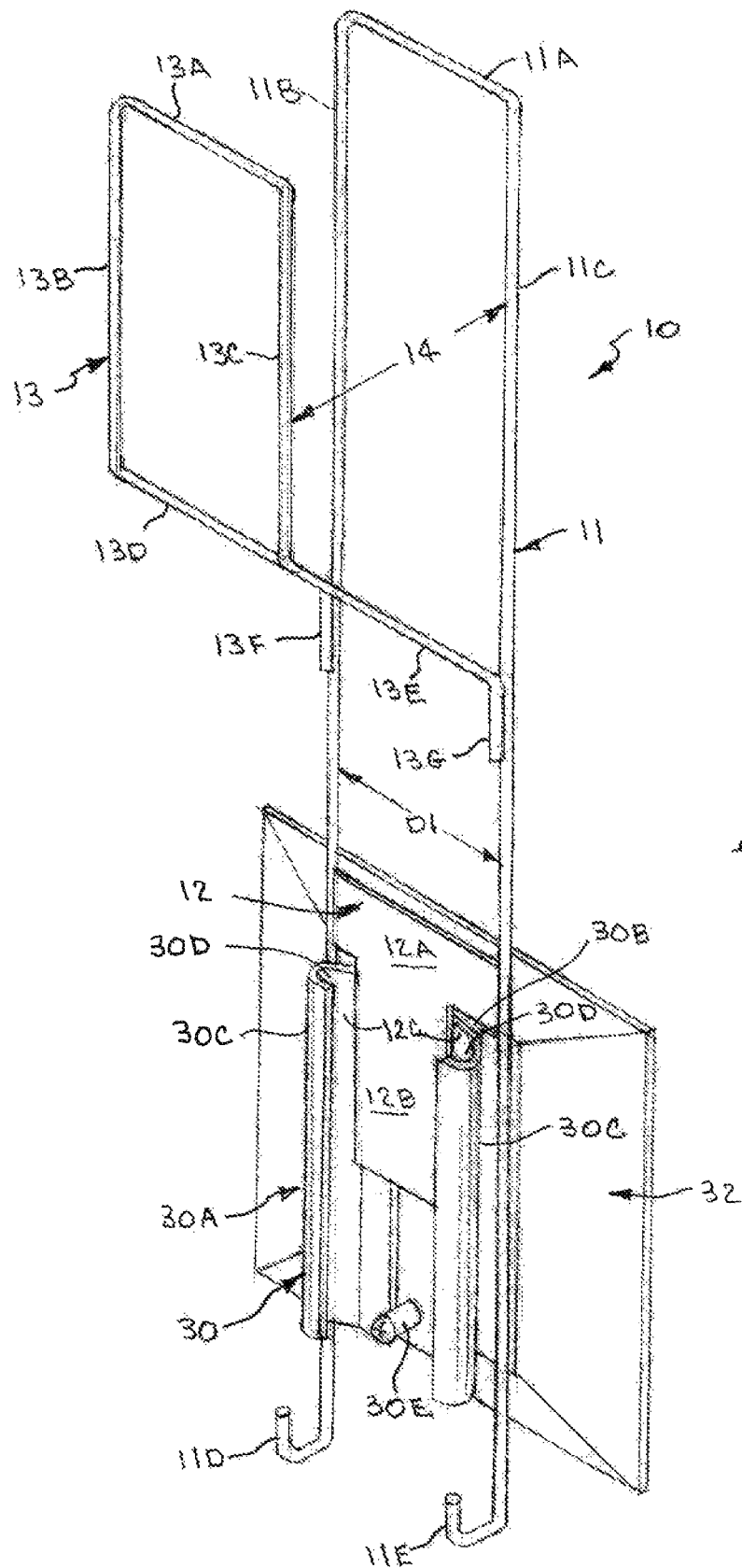
FIG. 2 is a perspective view of the storage rack mounted on the slide bracket.
Figure 3:
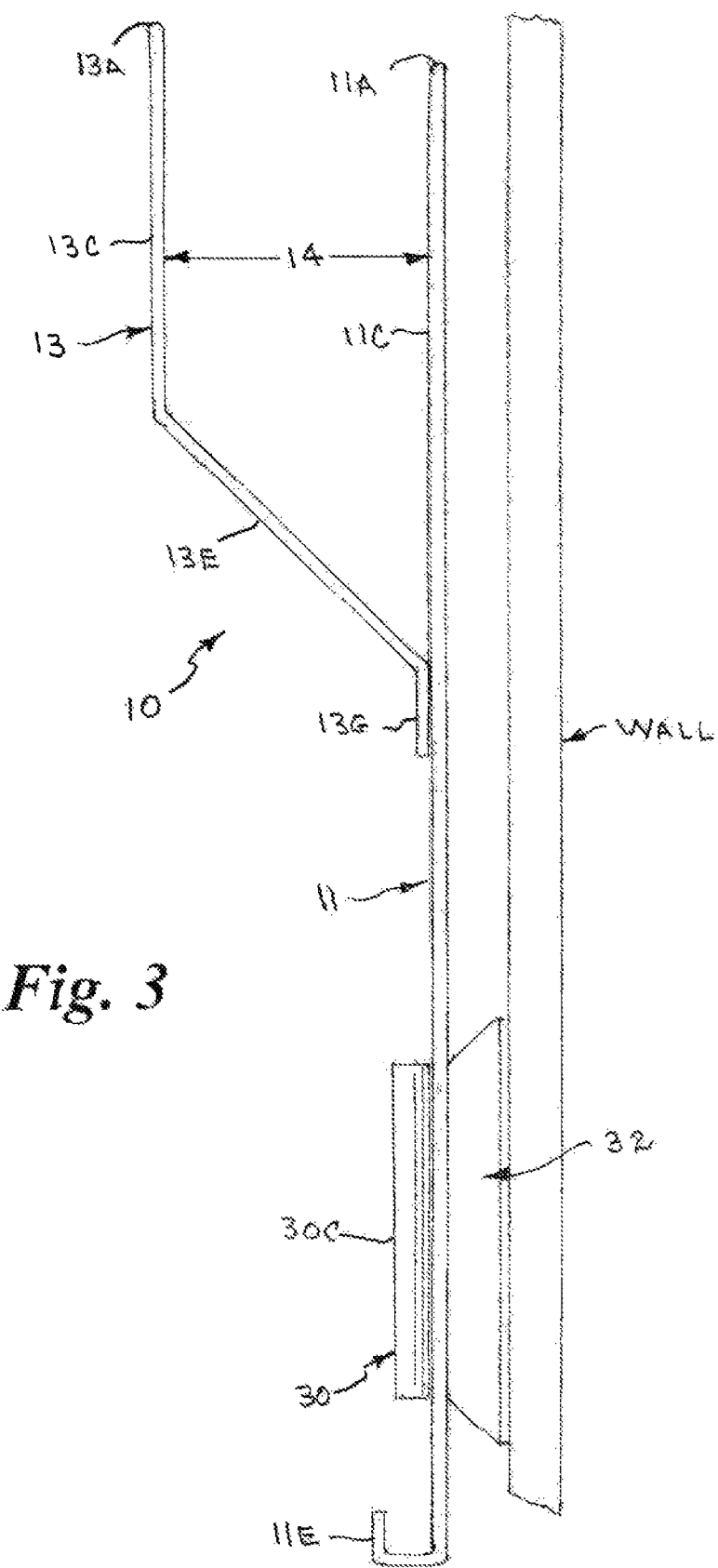
FIG. 3 is a side elevation view of the rack mounted on the slide bracket

Referring to the drawings by numerals of reference, there is shown in FIG. 1, a preferred embodiment of the storage rack 10 shown adjacent to a conventional medical slide bracket 30. As shown in FIGS. 2 and 3 and described hereinafter, the rack 10 is configured to be removably received on the slide bracket 30 and utilized for storing and supporting various accessory medical articles for reliable, rapid, ready access by medical personnel as needed. The storage rack 10 is best understood by first describing the structural features of the conventional slide bracket 30.

The slide bracket 30 is a commercially available product produced by several companies that provide gas suction and vacuum supplies to hospitals. They are typically mounted on the wall adjacent to the wall mounted gas outlets and flowmeters that protrude from the gas outlets. Some types may be mounted on a trim plate 32 affixed to the wall. The slide brackets 30 are characterized as having a generally rectangular body 30A with flat back wall 30B that engages the support surface (trim plate 32 or wall) and laterally opposed vertical curved sides 30C that curve outwardly and forwardly from the back wall and terminate in a short inwardly curved portion to form a pair of vertical channels 30D for slidably receiving a complementary engaging surface of a detachable medical accessory, such as a mounting bracket attached to a vacuum or suction container or canister (not shown) used to collect mucous, gas, or fluid aspirated from a patient. A slide stop means 30E, such as a lip or post extends a short distance forward and perpendicularly outwardly near the bottom of the bracket to support the bottom end of the complementary engaging surface of the detachable medical accessory such as a mounting bracket attached to the vacuum or suction container or canister. The back wall 30B and width between the outer curved sides of the vertical channels 30D of conventional slide brackets of different manufacturers is typically substantially the same.

The rack 10 includes a support member 11 and a holder member 13. The support member 11 is formed of rigid metal or plastic rod which is bent to form an elongated, inverted generally U-shaped configuration having a horizontal top portion 11A at the upper end, a pair of elongated laterally opposed leg portions 11B and 11C extending vertically downward from each end thereof, each of which terminates in an outwardly extending hook portion 11D and 11E. The laterally opposed leg portions 11B and 11C are spaced apart a sufficient distance Dl to closely straddle the vertical sides of the back wall back wall 30B of the slide bracket 30.

A thin flat T-shaped tab 12 is secured between laterally opposed leg portions 11B and 11C of the support member 11 a distance above the hook portions 11D and 11E. The tab 12 has a wider rectangular horizontal top portion 12A, the laterally opposed ends of which are secured to the laterally opposed leg portions 11B and 11C, and a narrower vertical lower portion 12B that extends vertically a distance downward from the underside of horizontal top portion 12A, defining a vertical slot 12C between each side of the narrower vertical lower portion 12B of the tab 12, respectively, and the laterally opposed leg portions 11B and 11C of the support member 11.

In the case of a rack formed of metal rod, the T-shaped tab 12 would also be formed of metal, and the laterally opposed ends of the top portion 12A may be secured to the laterally opposed leg portions 11B and 11C by conventional means such as welding; and in the case of a rack formed of plastic rod, the T-shaped tab 12 would also be formed of plastic, and the laterally opposed ends of the top portion 12A may be secured to the laterally opposed leg portions 11B and 11C by conventional means such as glue, epoxy, or ultrasonic welding.

The T-shaped tab 12 is dimensioned such that the narrower vertical lower portion 12B and vertical slots 12C of the tab may be slidably received in the slide bracket 30 between its outer curved sides 30C of the vertical channels 30D, and the underside of the wider rectangular horizontal top portion 12A of the tab 12 will engage and be supported on the on the top wall 30B or top ends of the outer curved sides 30C of the slide bracket.

The holder member 13 of the rack 10 is disposed above the T-shaped tab 12 which is fabricated of wire or plastic rod of the same diameter as the support member 11 and secured to the front thereof. The holder member 13 is bent to form an elongated, inverted generally U-shaped configuration having a horizontal portion 13A at the upper end, a pair of elongated laterally opposed upper leg portions 13B and 13C extending vertically downward a distance from each end thereof, each of which having an intermediate angular lower leg portion 13D and 13E, respectively, extending a distance angularly downwardly rearwardly therefrom terminating in short vertical leg portions 13F and 13G which are secured to the respective laterally opposed leg portions 11B and 11C of the support member 11 a distance above the T-shaped tab 12.

In the case of a rack formed of metal rod, the short vertical leg portions 13F and 13G may be secured to the laterally opposed leg portions 11B and 11C of the support member 11 by conventional means such as welding; and in the case of a rack formed of plastic rod, the short vertical leg portions 13F and 13G may be secured to the laterally opposed leg portions 11B and 11C of the support member 11 by conventional means such as glue, epoxy, or ultrasonic welding.

It should be understood from the foregoing that the intermediate angular lower leg portions 13D and 13E of the holder member 13 extend angularly upward and outward from the legs 11B and 11C of the support member 11 and the opposed upper leg portions 13B and 13C of the holder member extend upwardly and outwardly in parallel forwardly spaced relation relative to the legs 11B and 11C of the support member 11 and the horizontal top portion 13A at the upper end of the holder member is disposed a distance forward of the horizontal top portion 11A at the upper end of the support member 11.

The open area between the vertical upper leg portions 13B, 13C, and intermediate angular lower leg portions 13D, 13E, of the holder member 13 and the vertical legs 11B and 11C of the support member 11 define an open storage area 14 therebetween, and the hook portions 11D and 11E at the lower end of the legs 11B and 11C of the support member for removably receiving and supporting various articles.

The rack 10 is installed and removably supported on the slide bracket 30 by placing it above the slide bracket 30 and then lowering it downwardly such that: the laterally opposed leg portions 11B and 11C of the support member 11 straddle the flat back wall 30B and are received between the back wall and the outer curved sides of the slide bracket 30, the narrower vertical lower portion 12B of the T-shaped tab 12 is received in the slide bracket, and the vertical slots 12C of the tab are received between the outer curved sides 30C of the vertical channels 30D, and the underside of the wider rectangular horizontal top portion 12A of the tab 12 is engaged and supported on the top ends of the outer curved sides of the slide bracket.

When the rack 10 is installed on the slide bracket 30, the thin T-shaped tab 12 and the location and of the angular lower leg portions 13D and 13E of the holder member 13 at the front part of the rack 10 allow removal and replacement of a conventional vacuum canister on the slide bracket.

The open storage area 14 between the vertical upper leg portions 13B, 13C, and intermediate angular lower leg portions 13D, 13E, of the holder member 13 may be used for removably receiving and supporting various accessory medical articles. For example, the open storage area 14 may be used to store multiple and various sizes of bags and packaged items and make them readily available. Supplies bagged in drawstring bags and resuscitator bags as well as hoses and electrical cords may be hung from the hooked portions 11D and 11E at the bottom ends of the legs 11B and 11C of the support member 11.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A storage rack for removably mounting on a medical slide bracket of the type used to support a vacuum canister that collects mucous, gas, or fluid aspirated from a patient, the slide bracket having a flat back wall engaged on a support surface and laterally opposed vertical curved sides that curve outwardly and forwardly from the back wall terminate in an inwardly curved portion to form a pair of vertical channels, the storage rack comprising:

an elongated, inverted generally U-shaped support member formed of a rigid rod material having a horizontal top portion, a pair of elongated laterally opposed leg portions extending vertically downward from each end thereof and terminating in respective outwardly extending hook portions at a bottom end, and a flat T-shaped tab secured between the laterally opposed leg portions a distance above the hook portions;

an inverted generally U-shaped holder member formed of a rigid rod material having a horizontal portion at a top end, a pair of elongated laterally opposed upper leg portions extending vertically downward a distance from each end of the horizontal portion, each having an intermediate angular lower leg portion extending a distance angularly downwardly and rearwardly therefrom terminating in respective vertical leg portions secured to the laterally opposed leg portions of the support member a distance above the flat T-shaped tab;

the holder member horizontal portion, upper leg portions, and intermediate angular lower leg portions are disposed a distance forward of the horizontal top portion and the laterally opposed leg portions of the support member above the flat T-shaped tab, defining an open storage area between the holder member and the support member; and the elongated laterally opposed leg portions of the support member are configured to straddle the back wall of the slide bracket, the flat T-shaped tab secured between the laterally opposed leg portions is configured to engage and be supported on top ends of the laterally opposed vertical outer curved sides of the slide bracket, wherein the open storage area between the holder member and the support member, and the hook portions at the bottom end of the support member are adapted to receive and store medical supplies and equipment.

2. The storage rack according to claim 1, wherein the rigid rod material of said support member is metal, and the vertical leg portions of the holder member are secured to the laterally opposed leg portions of the support member by welding; and said flat T-shaped tab is formed of metal and welded between the laterally opposed leg portions of the support member.

3. The storage rack according to claim 1, wherein the rigid rod material of said support member is plastic, and the vertical leg portions of the holder member are secured to the laterally opposed leg portions of the support member by a securing means selected from the group consisting of glue, epoxy, and ultrasonic welding; and said flat T-shaped tab is formed of plastic and secured between the laterally opposed leg portions of the support member by a securing means selected from the group consisting of glue, epoxy, and ultrasonic welding.

\* \* \* \* \*